United States Patent [19]
Cougoulic

[11] Patent Number: 5,872,159
[45] Date of Patent: Feb. 16, 1999

[54] METHOD FOR PREPARING A MATERIAL FOR MEDICAL OR VETERINARY USE, RESULTING MATERIAL, AND USES THEREOF

[75] Inventor: Jean-Pierre Cougoulic, Pornichet, France

[73] Assignees: Julie Cougoulic; Linda Cougoulic, both of La Baule, France

[21] Appl. No.: 776,060

[22] PCT Filed: Jul. 24, 1995

[86] PCT No.: PCT/FR95/00993

§ 371 Date: Feb. 18, 1997

§ 102(e) Date: Feb. 18, 1997

[87] PCT Pub. No.: WO96/03161

PCT Pub. Date: Feb. 8, 1996

[30] Foreign Application Priority Data

Jul. 22, 1994 [FR] France .................................. 94 09246

[51] Int. Cl.⁶ ............................ A61F 2/02; A61C 13/00; C08K 3/32; B28B 3/20
[52] U.S. Cl. ...................... 523/115; 524/417; 264/176.1; 264/211; 264/328.18
[58] Field of Search ............................ 523/115; 524/417; 264/176.1, 211, 328.18

[56] References Cited

U.S. PATENT DOCUMENTS

| | | |
|---|---|---|
| 4,645,503 | 2/1987 | Lin et al. . |
| 4,863,974 | 9/1989 | Mallouk et al. . |
| 5,246,457 | 9/1993 | Piez et al. .............................. 264/122 |
| 5,290,494 | 3/1994 | Coombes et al. ...................... 264/216 |
| 5,425,770 | 6/1995 | Piez et al. .............................. 264/122 |
| 5,639,402 | 6/1997 | Barlow et al. .......................... 264/430 |

FOREIGN PATENT DOCUMENTS

| | | |
|---|---|---|
| 0 026 090 | 4/1981 | European Pat. Off. . |
| 0 171 884 | 2/1986 | European Pat. Off. . |
| 0 378 102 | 7/1990 | European Pat. Off. . |
| 28 21 354 | 11/1978 | Germany . |

*Primary Examiner*—Peter A. Szekely
*Attorney, Agent, or Firm*—Young & Thompson

[57] ABSTRACT

A method for preparing a material for medical or veterinary use by uniformly mixing a thermoplastic polymer, preferably polyether etherketone (PEEK), at least with tricalcium phosphate ($Ca_3(PO_4)_2$), and injection or extrusion moulding the resulting mixture under conditions suitable for converting the tricalcium phosphate into calcium hydroxyapatite. The basic mixture preferably comprises a biocompatible metal oxide such as titanium dioxide ($TiO_2$). The resulting material is useful for making endosseous implants or bone prostheses.

9 Claims, 6 Drawing Sheets

METHOD FOR PREPARING A MATERIAL FOR MEDICAL OR VETERINARY USE, RESULTING MATERIAL, AND USES THEREOF

FIELD OF THE INVENTION

This invention relates to a process for obtaining a material for medical or veterinary uses, designed especially, but not exclusively, for the execution of endo-osseous implants, notably dental ones, or the execution of osseous prosthesis. The invention also relates to the material obtained by the process as well as its applications.

BACKGROUND OF THE INVENTION

Numerous types of materials, either metallic or plastic, are used in the medical or veterinary field, for the replacement of biological structures (bones especially) or the fixation of functional organs (dental implants or others, . . .).

The selection of the material is made in relation to its structural intrinsic characteristics and also in relation to its biocompatibility, in terms of integration or, what is better, in terms of biological tolerance.

For informative purposes, the document EP-A-0378102 describes an implantation material obtained by extrusion moulding of a thermoplastic polymer mixture with calcium hydroxyapatite and additional charging constitutive elements.

The document US-A-4645503 suggests a bone reparation material comprising a biocompatible and biodegradable thermoplastic polymer, mouldable at ordinary temperature and mixed with a filler, preferably calcium hydroxyapatite, tricalcium phosphate or glass granules, used alone or in combination.

SUMMARY OF THE INVENTION

The purpose of the present invention is to offer a cheap and easy to implement process, enabling to obtain a material which combines good general mechanical qualities and excellent biocompatibility in terms of biological tolerance, liable to allow particularly efficient usage in the medical and veterinary fields.

Another purpose of the invention is to offer a process allowing to obtain a material whose constitution is close to that of the bone.

The process complying with the present invention consists in mixing homogeneously a biocompatible thermoplastic polymer with tricalcium phosphate ($Ca_3(PO_4)_2$). The mixture obtained then undergoes an injection or extrusion type moulding operation, under suited conditions (especially temperature and pressure) to ensure the transformation of the tricalcium phosphate into calcium hydroxyapatite ($Ca_5(PO_4)_3OH$).

The transformation during the moulding operation is performed according to the following reaction:

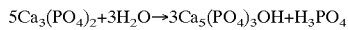
$5Ca_3(PO_4)_2 + 3H_2O \rightarrow 3Ca_5(PO_4)_3OH + H_3PO_4$

The presence of calcium hydroxyapatite allows the moulded material to come close to the natural composition of the bone in order to enhance its biocompatibility.

In addition to the calcium hydroxyapatite formed out of the tricalcium phosphate, one can expect to add a small proportion to the basic mixture, before moulding.

The above reaction is carried out partially and the moulded end-product contains residual tricalcium phosphate.

Tricalcium phosphate is one of the basic biological compounds for the formation of calcium hydroxyapatite; it also exhibits a healing function and it is resorbable.

Orthophosphoric acid ($H_3PO_4$) as such is prescribed as calcium fixative and as acidifying agent; this therapy is little active; however, it enjoys newly found favours by the use of high doses of alkaline phosphates and of glycerophosphates in affections where the calcium metabolism is disturbed. The orthophosphoric acid is a fundamental constitutive element of the nucleotides: a nucleotide is formed of a puric or pyrimidic basis to which has been attached by a glucosidic link a sugar combined to a molecule of phosphoric acid. Nucleotide is the basis unit of the nucleic acids. Nucleic acids combined to one or several protein molecules produce nucleoproteins, which constitute an important part of the cores of the cells and can also be traced in the cytoplasm. Thus, phosphorus is a fundamental element of living matter and of biochemistry.

Orthophosphoric acid ($H_3PO_4$) is derived from the transformation process of tricalcium phosphate into calcium hydroxyapatite; this product is volatile, but it remains present in the moulded end-material. Possibly, it may be added to the basic mixture, before moulding.

The biocompatible thermoplastic polymer has a linking function; it has been chosen for its physical properties after forming. For exemplification purposes, one can use a polyether-etherketone, as polyether-ketone, a polysulfone, a polytetrafluoro-ethylene, a polyether-block-amids or a polyimide.

Due to its YOUNG's modulus and to its interesting structure characteristics, close to those of the bone, polyether-etherketone (PEEK) will be used preferably. PEEK is a semi-crystalline polymer formed of an aromatic linear chain based on the repetition of the following units:

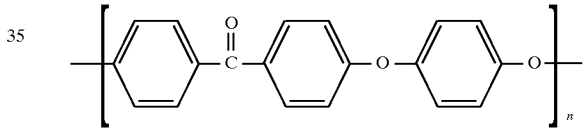

The characteristics of this polymer are detailed in the commercial leaflet published in 1992 by the ICI MATERIALS Company "Victrex PEEK, the high temperature engineering thermoplastic—Properties and processing."

Moreover, the basic composition, before moulding, may advantageously comprise one or several agents liable to foster the formation of calcium hydroxyapatite and/or liable to improve the radio-opacity of the moulded mixture. One can thus add one or several biocompatible metallic oxides, selected among ceramics such as titanium dioxide ($TiO_2$), zirconium dioxide ($ZrO_2$) or aluminium oxide ($Al_2O_3$).

The disinfecting side effect of titanium dioxide can be an important criterion of selection.

These metallic oxides can play a catalysing role in the chemical reaction; they exhibit a high molar mass which will enable to reinforce the radio-opacity of the thermoplastic.

The material according to the invention is formed by moulding, injection or extrusion type, of a homogeneous mixture of constitutive elements. The material and the moulding conditions are suited to this mixture and especially to the basic thermoplastic.

The starting homogeneous mixture contains tricalcium phosphate, a compound capable of being transformed into calcium hydroxyapatite during the moulding operation in combination with the kneading action of the wormgear and the temperature and pressure rises; ice may also contain calcium hydroxyapatite in the form of $Ca_{10}(PO_4)_6 OH_2$, as well as one or several metallic oxides.

In order to keep a mouldable material with the desired behaviour and resistance, the thermoplastic polymer represents at least 65% in weight of the end-material. On the other hand, in order to bring enough chemical elements designed for fostering biological integration, the additional components (tricalcium phosphate, calcium hydroxyapatite and metallic oxide ($TiO_2$)) will represent between 10 and 35% in weight of the end-material.

Obviously, for particular application, the proportions of the materials implied may differ.

A good compromise, especially in terms of mechanical properties (hardness, resilience, tensile, deflection and torsion behaviour) will correspond to more or less 80% of thermoplastic polymer and 20% of additional components.

DETAILED DESCRIPTION OF THE INVENTION

EXAMPLES

Figure 1:
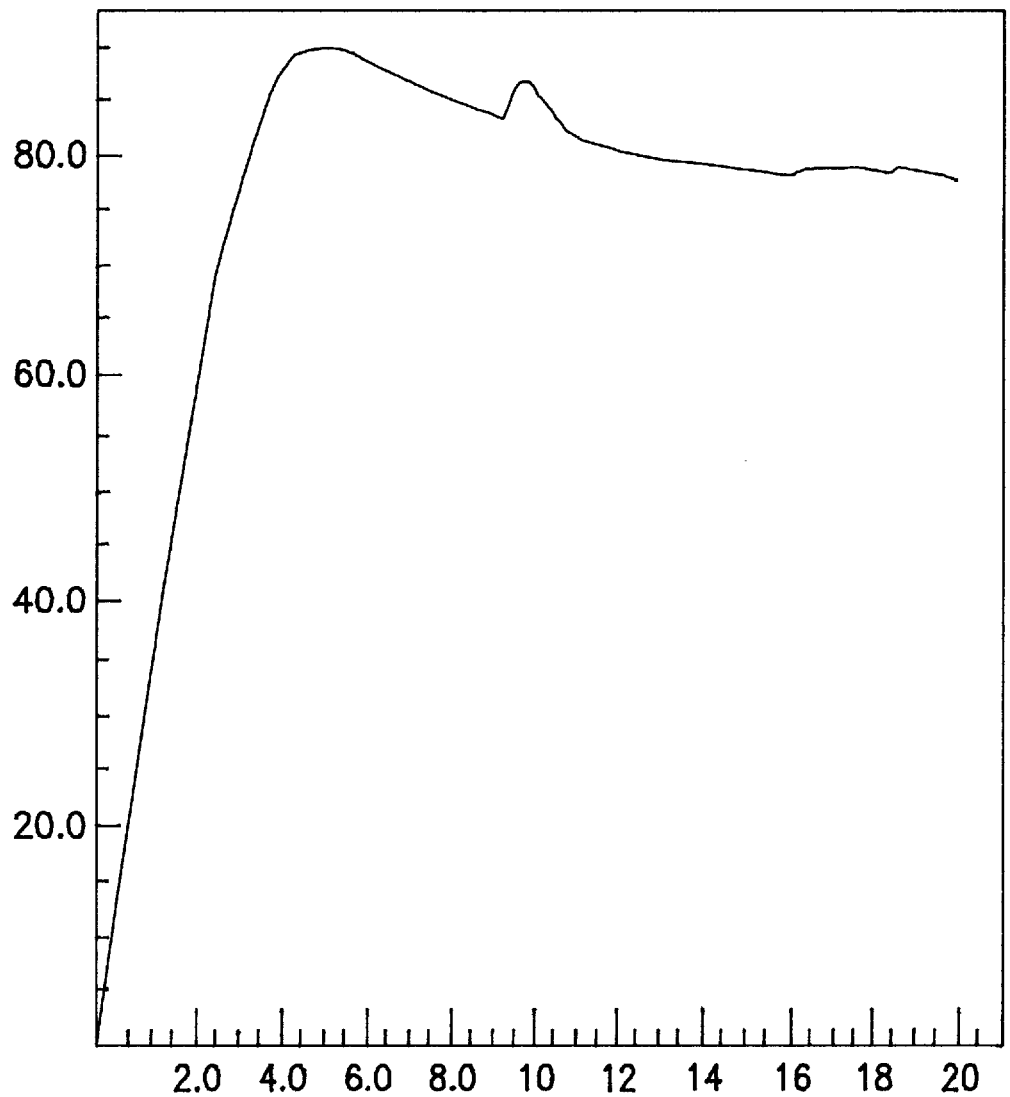

Basic mixtures are performed out of polyetheretherketone (PEEK), calcium dihydroxyapatite, tricalcium phosphate ($Ca_3(PO_4)_2$) and titanium dioxide ($TiO_2$).

Another basic mixture is performed out of polyetheretherketone (PEEK), tricalcium phosphate ($Ca_3(PO_4)_2$) and titanium dioxide ($TiO_2$).

PEEK is available in the form of powder or granules (size: approx. 100 microns), distributed by the THERTEC SA Company, 78370 PLAISIR-FRANCE; the reference of the PEEK used is "450 G pf", this especially because of its presentation in terms of granulometry, in order to optimize the mixture with the other constitutive elements.

The calcium dihydroxyapatite used is distributed by BIOLAND SARL, 31100 TOULOUSE-FRANCE; it is available in the form of a white powder.

The tricalcium phosphate is available in powder form (grains of size in the order of 200 microns); it is for instance marketed by the Coopération Pharmaceutique Francaise, S.A., 77020 MELUN-FRANCE.

The titanium dioxide is also available in the form of a powder distributed by the Coopération Pharmaceutique Francaise, S.A., 77020 MELUN-FRANCE.

a) Proportions

The components above are present in the following proportions:

Mixture 1 (10% loads)
  PEEK: 90% in weight
  Ca3 (PO4)2: 4% in weight
  TiO2: 4% in weight
  Ca10 (PO4)6 OH2: 2% in weight
Mixture 2 (20% loads)
  PEEK: 80% in weight
  Ca3 (PO4)2: 9% in weight
  TiO2: 9% in weight
  Ca10 (PO4)6 OH2: 2% in weight
Mixture 3 (30% loads)
  PEEK: 70% in weight
  Ca3 (PO4)2: 14% in weight
  TiO2: 14% in weight
  Ca10 (PO4)6 OH2: 2% in weight
Mixture 4 (35% loads)
  PEEK: 65% in weight
  Ca3 (PO4)2: 16.5% in weight
  TiO2: 16.5% in weight
  Ca10 (PO4)6 OH2: 2% in weight
Mixture 5
  PEEK: 80% in weight
  Ca3 (PO4)2: 10% in weight
  TiO2: 10% in weight b) Kneading The constitutive elements of each mixture are placed in a turbine mixer until perfect homogenization.

c) Drying

Each mixture obtained is dried in an air circulation stove for 3 hours at 150° C.

d) Moulding

The moulding operation is performed on a KRAUSS-MAFFEI type injection press, model 90-340-32, KRAUSS MAFFEI FRANCE, 92632 GENNEVILLIERS-FRANCE.

The preparation conditions of the material and the moulding conditions of the mixture correspond to those used for the pure PEEK, in compliance with the commercial leaflet "ICI MATERIALS" introduced above.

As the PEEK is a semi-crystalline thermoplastic, it is necessary to heat the mould, failing which the surface finish of the moulded parts would be negatively affected. Indeed, the surface veil would be in an amorphous phase and the core in a crystalline phase; if the mould were too cold, the parts could even taken on a totally amorphous character and the mechanical characteristics would drop severely.

Thermal control of the mould is ensured by an oil re-heater enabling to maintain it at a temperature of approx. 160° C. Insulation means limit thermal dispersions and preserve the peripheral organs of the injection press. These means can be insulating plates formed of a complex of glass fibre.

For series injections, a vibrator shall be advantageously fixed on the sieve in order to foster the flowing of the mixture.

Generally, the moulding is performed at a temperature comprised between 340° and 400° C. and at an injection pressure from 70 to 140 MPa.

The form of the mould can vary in relation to the part that one wishes to obtain, for instance for the execution of an osseous prosthesis, notably for orthopedic applications. One can also obtain a bloc of matter that will be then cut or machined according to the shape desired, for osseous filling or an implant, of a dental type for instance. According to the applications foreseen, one could also integrate the execution of filaments which, after knitting or weaving, will be used as a jacket, protection or support membrane.

Results a) Mechanical tests tensile test

These tests have been carried out on a tensile machine INSTRON, Model 4302, INSTRON S.A., 78284 GUYANCOURT-FRANCE.

The test pieces used have a cross section of 40 mm and a length between jaws of 80 mm, The stress are measured in relation to the deformation percentages; the results appear on the curves of FIGS. 1 to 5 with the deformation (%) in abscissae and the stress (MPa) as an ordinate.

Figure 2:
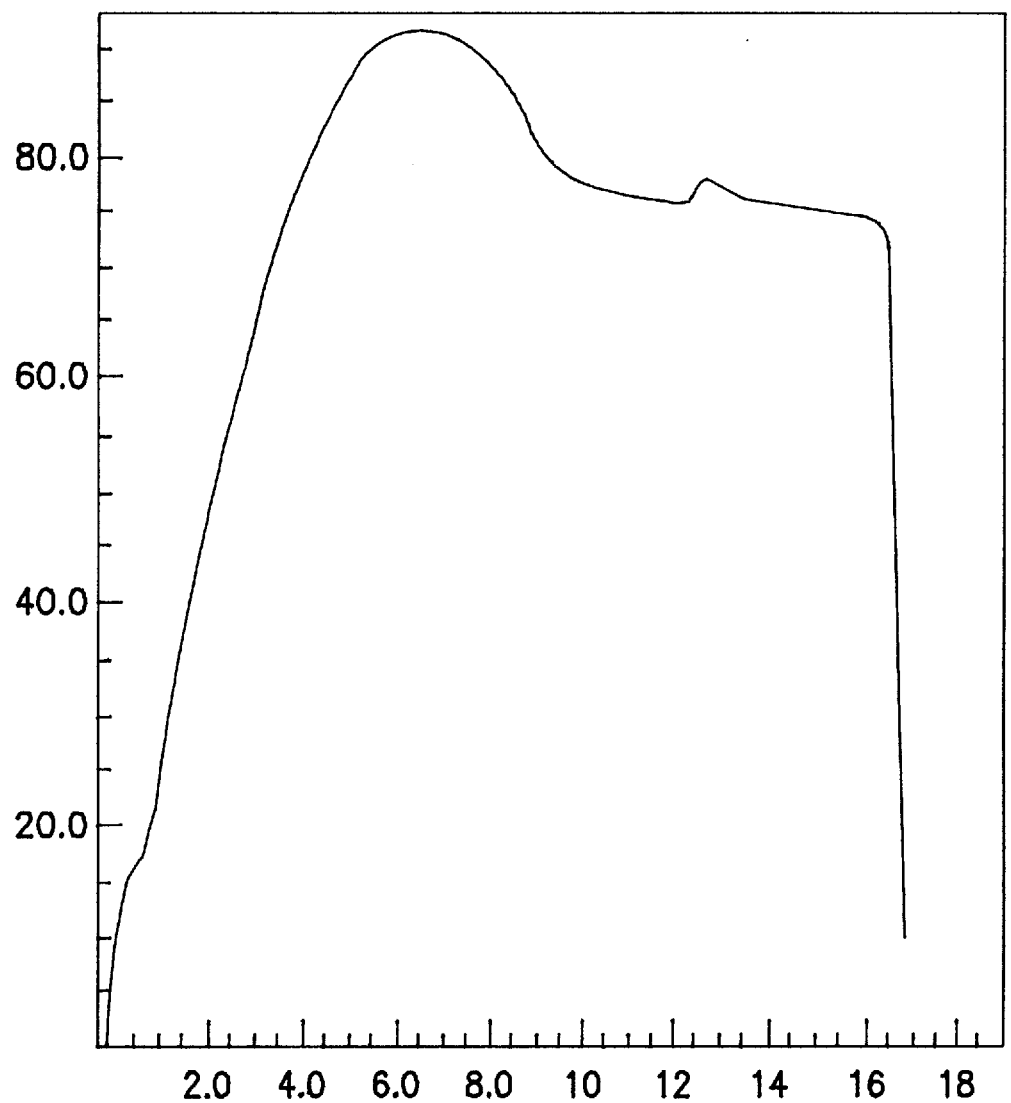
Figure 3:
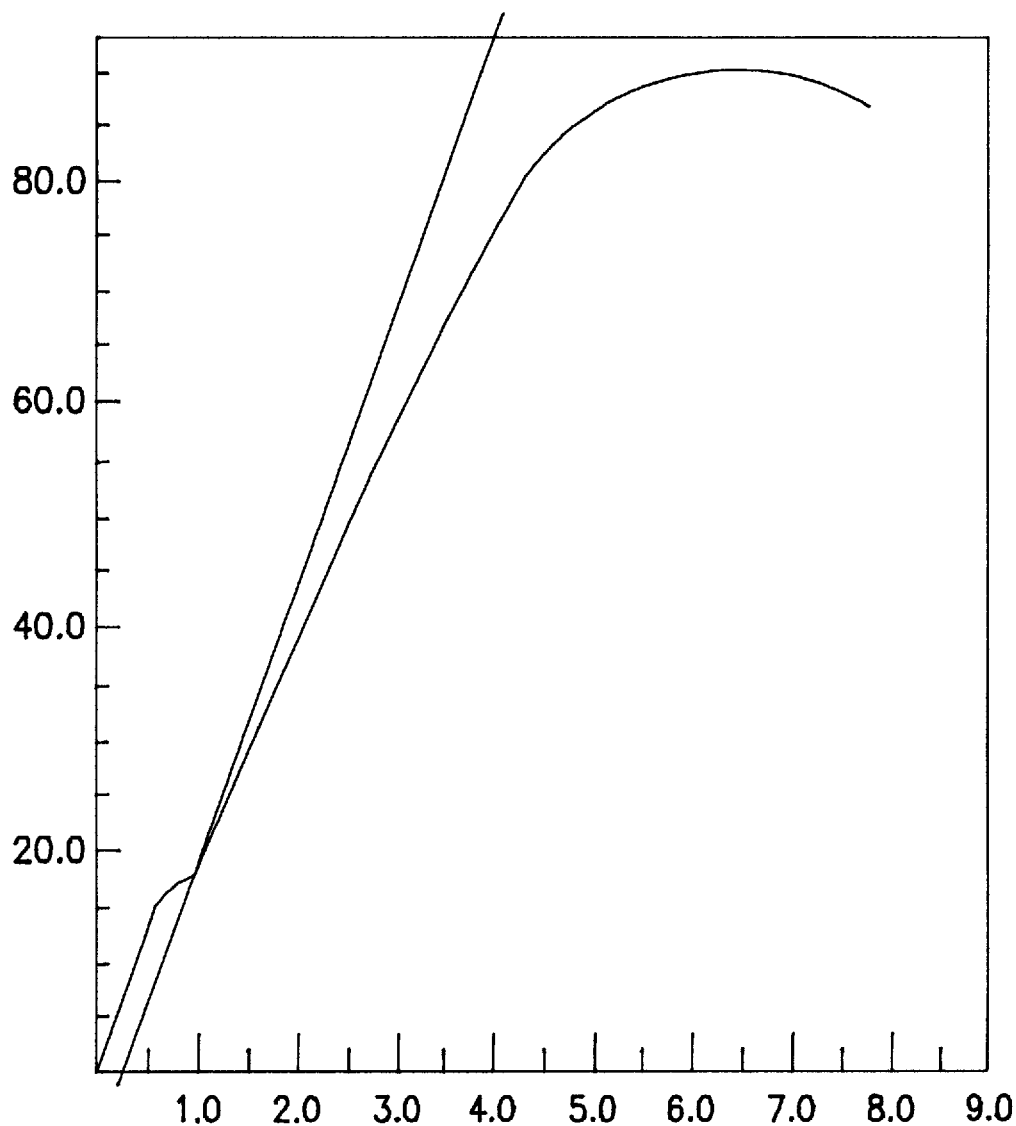
Figure 4:
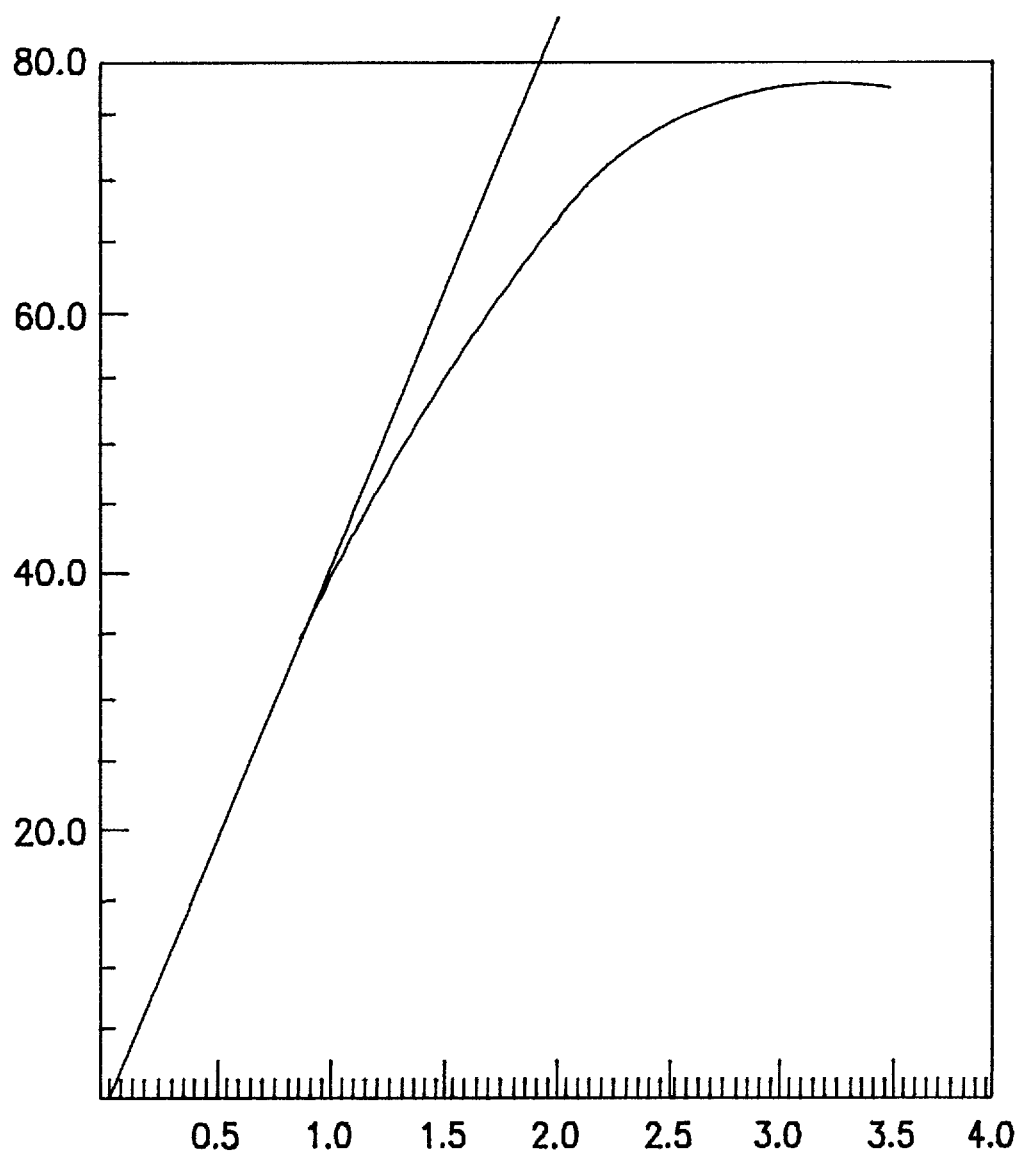
Figure 5:
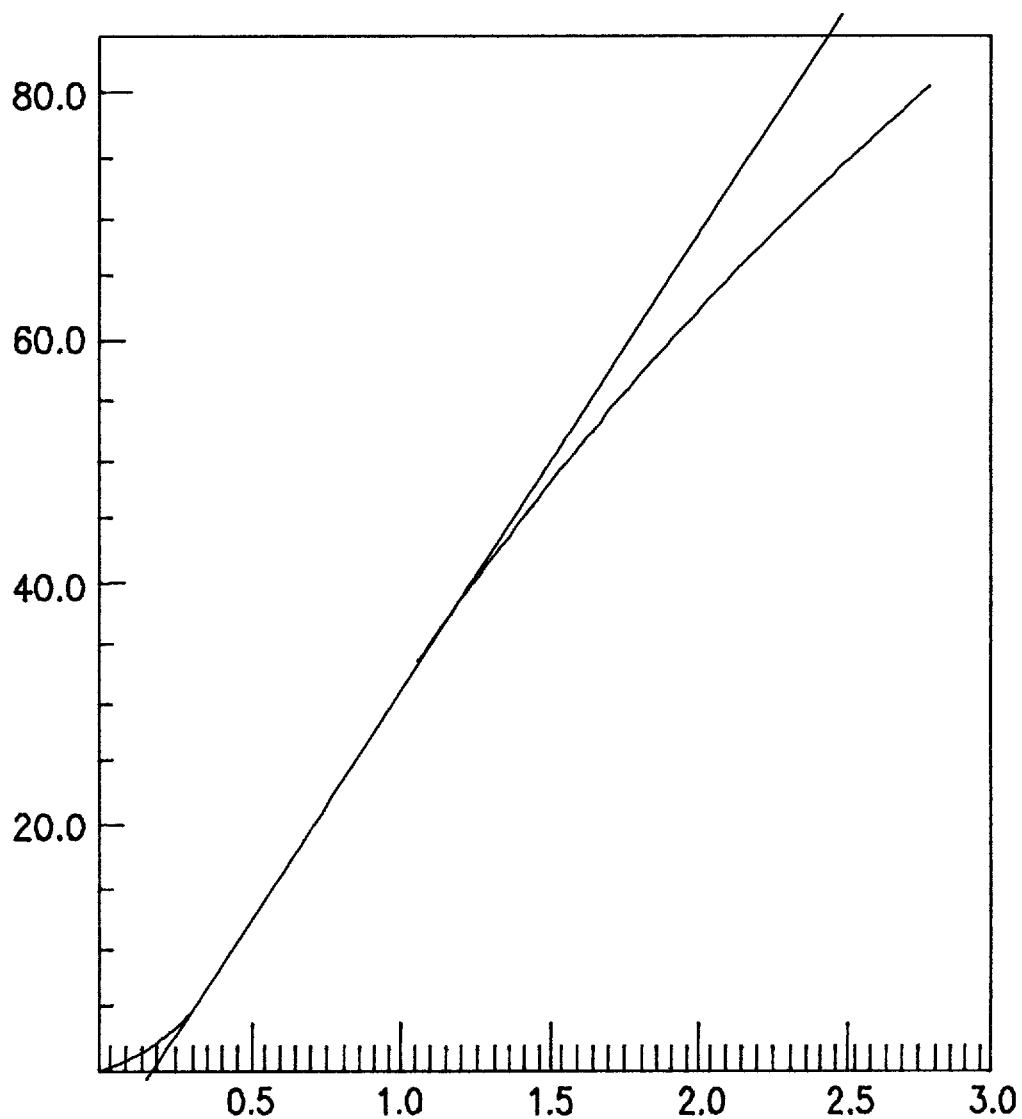

FIG. 1 corresponds to a test on pure PEEK;
  FIG. 2 corresponds to the test on mixture 1;
  FIG. 3 corresponds to the test on mixture 2;
  FIG. 4 corresponds to the test on mixture 3 and
  FIG. 5 to the test on mixture 4.

From the curves obtained, the tangent modulus of the material can be determined which is the original slope of the curve.

The results are shown on the tables hereunder where:
E: tangent modulus
SgM: maximum stress
SgR: breaking stress
SgP: stress beyond the limit of proportionality
A: maximum elongation

|  | E (MPa) | SgM (MPa) | SgR (MPa) | SgP (MPa) | A (mm) |
|---|---|---|---|---|---|
| | | Pure PEEK | | | |
| Mean | 2525 | 95.7 | 77.7 | 38.9 | 35.09 |
| Standard deviation | 66 | 2.6 | 3.3 | 2.35 | 11.27 |
| | | 10% mixture | | | |
| Mean | 2577 | 90.6 | 70.8 | 36.7 | 12.16 |
| Standard deviation | 126 | 1.13 | 1.13 | 2.4 | 0.78 |
| | | 20% mixture | | | |
| Mean | 2967 | 90 | 83 | 35 | 5.63 |
| Standard deviation | 45 | 0 | 6.4 | 0 | 0.51 |
| | | 30% mixture | | | |
| Mean | 3637 | 76.2 | | 37.5 | 3 |
| Standard deviation | 47.5 | 2.8 | | 2.5 | 1 |
| | | 35% mixture | | | |
| Mean | 3684 | 75.7 | | 33.3 | 2.11 |
| Standard deviation | 35.3 | 6.1 | | 2.4 | 0.19 |

The pure PEEK and the 10% mixture exhibit the behaviour of a visco-elastic thermoplastic with a threshold. The 20% mixture has a visco-elastic behaviour without threshold; the 30 and 35% ones have a fragile behaviour.

As a summary, the larger the load, the more the compound resists deformation, but the more brittle it is.

resilience test

The resilience tests have been carried out on a pendulum rack impact testing machine of CEAST make, model 6548, ADAMEL LHOMARGY Company, 94203 IVRY SUR SEINE-FRANCE. The method selected is that of the Charpy pendulum rack impact testing machine. The purpose is to measure the resistance to shocks in Kj/m.

The resistance to shocks is given by the relation: $R = E/S$ with $E$ = absorbed energy and $S$ = cross section of the test-piece (40 mm).

After test, the following results are obtained:

| Load % | 0 | 10 | 20 | 30 | 35 |
|---|---|---|---|---|---|
| Mean E (J) | 30.8 | 18.36 | 3.39 | 2.34 | 1.61 |
| E (J) standard deviation | 4.8 | 1.35 | 0.47 | 0.11 | 0.15 |
| R (kJ/m**) | 770 | 459 | 84.8 | 58.45 | 40.2 | with mean E: energy absorbed during the shock
R: resistance to the shock in kJ/m**

It appears that the more the load increases in the mixture, the less the former resists to shocks. This reduction is more progressive from 20 to 35% of loads, whereas the value drop drastically from 0 to 20% of loads.

flexural test

The method used is the vibratory flexure with three embedding links and temperature sweep, called "Dual cantilever". These tests have been carried out on a visco-elasticimeter Rhéométrics, RSA II type, RHEOMETRICS FRANCE, 77436 MARNE LA VALLEE-FRANCE.

The purpose is to determine the flexural modulus E' in relation to temperature. Sweeping enables, among other things, to visualise the vitreous transient temperature beneath which it is necessary to remain during machining. It is characterised by a drop of the flexural modulus.

The following table exhibits, for a given temperature, the value of the flexural modulus E' for a certain load of the mixture.

| Load % | Temperature (°C.) | E' (MPa) |
|---|---|---|
| 0 | 31.79 | 3300 |
| 10 | 29.48 | 2781.1 |
| 20 | 31.3 | 3117.8 |
| 30 | 30.68 | 3865.2 |
| 35 | 31.31 | 3717.1 |

A drop of the modulus value for the 10% mixture can be noticed, then a constant progression for the following loads before a slight degradation for the 35% mixture.

torsional test

A tensile machine INSTRON (model 4302, INSTRON S.A., 78284 GUYANCOURT-FRANCE) is used, as well as a mechanical device which transforms the tensile movement into rotation. The latter is turned into a mechanical welding apparatus thanks to a precision assembly. Torquing and angular values are then derived from the force and displacement values.

The purpose is to determine the shear modulus G, commonly called the modulus of COULOMB.

The tests are performed on cylindrical pieces, 8 mm in diameter and 40 mm in length.

In the result tables below:
G: modulus of elasticity in shear (Coulomb)
Cmax: maximum torque
Cadm: maximum admissible torque
$\mu$: angular/length limit

|  | G (MPa) | Cmax (N · m) | Cadm (N · m) | $\mu$ (°/mm) |
|---|---|---|---|---|
| | Pure PEEK | | | |
| Mean | 1190.5 | 8.13 | 3.17 | 2.25 |
| Standard deviation | 48.1 | 0.13 | 0.23 | 0.1 |
| | 10% mixture | | | |
| Mean | 1185 | 7.18 | 3.08 | 2.34 |
| Standard deviation | 57 | 0.02 | 0.12 | 0.14 |
| | 20% mixture | | | |
| Mean | 1475 | 7.52 | 3.33 | 2.57 |
| Standard deviation | 34.4 | 0.02 | 0.12 | 0.01 |
| | 30% mixture | | | |
| Mean | 1763 | 8.75 | 2.83 | 1.9 |
| Standard deviation | 58 | 0.35 | 0.31 | 0.3 |
| | 35% mixture | | | |
| Mean | 1738 | 5.26 | 2.28 | 0.625 |
| Standard deviation | 107.6 | 1.13 | 0.33 | 0.26 |

It can be observed that the heavier the load, the more resistant the sample to the torsional stresses. However, the shear modulus at 10% is not higher than that of the pure PEEK, if even slightly lower; on the other hand, the 35% mixture is less resistant than the 30% one.

hardness test

The BRINELL hardness method is employed (measurement of the mark left by the penetration of a steel ball). The test is performed on a durometer ISSER STEDT, model Dia testor 2 RC, CONTROLAB company, 93400 ST OUEN-FRANCE.

The measurements are carried out with two different standard pressures (15.625 and 31.25 Kp). The dispersions are very low.

The results are given in the table below:

| Load % | 0 | 10 | 20 | 30 | 35 |
|---|---|---|---|---|---|
| Brinell hardness | 26.4 | 20.3 | 25.8 | 30.9 | 33.3 |
| Standard deviation | 0.24 | 0.54 | 1.1 | 0.79 | 0.44 |

It should be noted that the heavier the load, the more resistant the material becomes, with the exception of the 10% mixture which proves softer that pure PEEK.

These various results show that the 20% mixture seems a good mechanical compromise; it exhibits characteristics close to those of pure PEEK as well as reasonable resilience. It is hard and ductile at the same time.

b) test of chemical analysis

Figure 6:
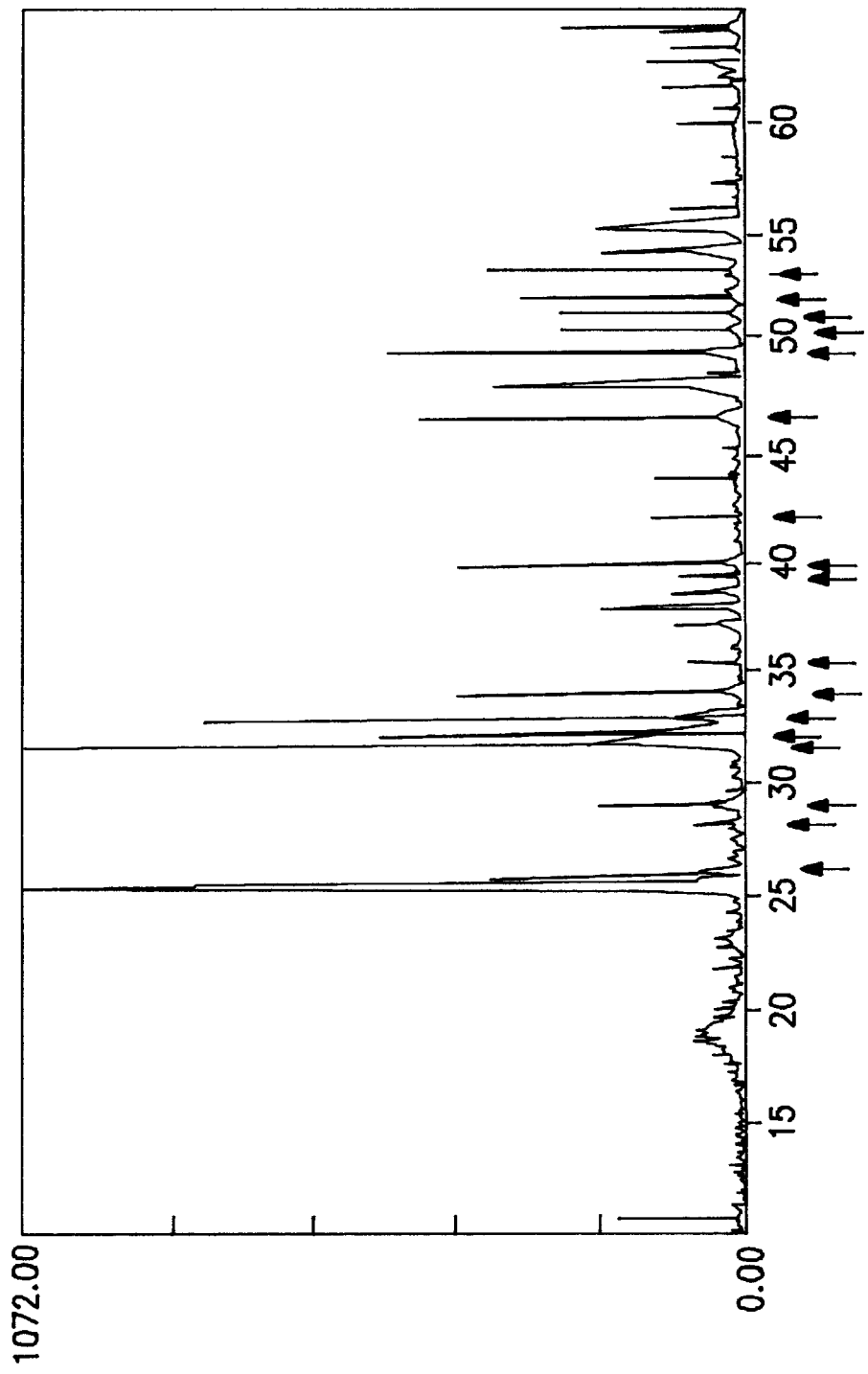

FIG. 6 shows the diffraction spectrum X of mixture number 5, i.e. comprising of PEEK (80%), tricalcium phosphate (10%) and titanium dioxide (10%).

The presence of peaks put in evidence by the arrows indicates the presence of calcium hydroxyapatite in the moulded material.

c) experimental validation

The moulded material obtained according to the example above has been machined in order to execute a dental implant with end drill bit and thread, designed to be screwed into the jaw. This implant has been installed with a knurled screwdriver. Using a lever arm fitted with gauges, the tightening torque has been raised to 1.2 Nm (whereas the maximum tightening torque exerted by a practicioner on the screwdriver is estimated at 0.6 Nm).

After removal, the observation of these implants shows that the edges of the end drill bit do not exhibit any breakage nor blatant wear. Moreover, no angular deformations due to the screwing action could be noticed.

On the other hand, after analysis, it appears that the human tissues and cells have accepted the implant extremely well from a biological viewpoint.

I claim:

1. A process for obtaining a moulded material, comprised of a biocompatible thermoplastic polymer with hydroxyapatite, for medical or veterinary uses, which comprises:

homogeneously mixing the biocompatible thermoplastic polymer at least with tricalcium phosphate ($Ca_3(PO_4)_2$) to obtain a mixture; and subjecting the mixture to an injection or extrusion moulding operation under conditions suited to ensure transformation of the tricalcium phosphate into calcium hydroxyapatite and into orthophosphoric acid.

2. A process according to claim 1, wherein the thermoplastic polymer is mixed at a ratio of 65 to 90% by weight, with 10 to 35% by weight of additional components.

3. A process according to claim 1, wherein the thermoplastic polymer used consists of polyether etherketone (PEEK).

4. A process according to claim 1, further comprising incorporating to the mixture, before moulding, at least one biocompatible metallic oxide selected from the group consisting of titanium dioxide, zirconium dioxide and aluminum oxide.

5. A process according to claim 4, wherein the metallic oxide used is titanium dioxide ($TiO_2$).

6. A process according to claim 1, wherein the mixture comprises:

polyether etherketone (PEEK);
   tricalcium phosphate ($Ca_3(PO_4)_2$); and
   titanium dioxide ($TiO_2$).

7. A process according to claim 6, wherein the mixture comprises:

80% by weight of polyether etherketone;
   10% by weight of tricalcium phosphate; and
   10% by weight of titanium dioxide.

8. A material for biological or medical uses obtained by the process according to claim 1.

9. A material according to claim 8, comprising:

65 to 90% by weight of thermoplastic polymer;
   10 to 35% by weight of additional components, in the form of calcium hydroxyapatite associated with tricalcium phosphate and with orthophosphoric acid.

* * * * *